United States Patent [19]

Wollweber et al.

[11] Patent Number: 4,963,181
[45] Date of Patent: Oct. 16, 1990

[54] FUNGICIDAL 3-CYANO-4-PHENYL-PYRROLE DERIVATIVES

[75] Inventors: Detlef Wollweber, Wuppertal; Wilhelm Brandes, Leichlingen; Stefan Dutzmann, Duesseldorf, all of Fed. Rep. of Germany

[73] Assignee: Bayer Aktiengesellschaft, Leverkusen, Fed. Rep. of Germany

[21] Appl. No.: 337,195

[22] Filed: Apr. 12, 1989

[30] Foreign Application Priority Data

Apr. 29, 1988 [DE] Fed. Rep. of Germany ....... 3814479

[51] Int. Cl.$^5$ ........................................... C07D 207/44
[52] U.S. Cl. ....................... 71/95; 548/430; 548/431
[58] Field of Search ................ 514/423; 548/430, 431; 71/95

[56] References Cited

U.S. PATENT DOCUMENTS

| 4,229,465 | 10/1980 | Ohkuma et al. | 514/423 |
| 4,303,667 | 12/1981 | Ueda et al. | 514/423 |
| 4,705,801 | 11/1987 | Martin et al. | 514/423 |

FOREIGN PATENT DOCUMENTS

| 0174910 | 3/1986 | European Pat. Off. |
| 0206999 | 12/1986 | European Pat. Off. |
| 0236272 | 9/1987 | European Pat. Off. |
| 2927480 | 1/1980 | Fed. Rep. of Germany |

*Primary Examiner*—Mary C. Lee
*Assistant Examiner*—Catherine Scalzo
*Attorney, Agent, or Firm*—Sprung Horn Kramer & Woods

[57] ABSTRACT

Fungicidal 3-cyano-4-phenyl-pyrrole derivatives of the formula

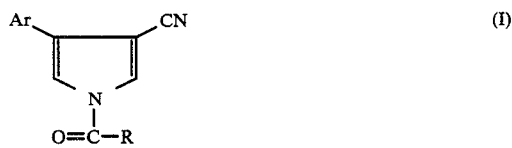

in which

Ar stands for phenyl which is trisubstituted to pentasubstituted and

R stands for alkyl, alkoxy or alkoxyalkyl.

Claimed are compounds of the formula (I) wherein Ar is phenyl which is trisubstituted by halogen, at least one of which is fluorine, and R is alkyl, alkoxy or alkoxyalkyl each having 1 to 6 carbon atoms in the individual alkyl moieties, fungicidal compositions containing the compounds, and a method of combating fungi comprising administering the compounds to the fungi or their habitat.

9 Claims, No Drawings

FUNGICIDAL 3-CYANO-4-PHENYL-PYRROLE DERIVATIVES

The invention relates to new 3-cyano-4-phenylpyrrole derivatives, a process for their preparation and their use in pesticides.

It is known that certain 3-cyano-4-phenylpyrroles, such as, for example, the compound 3-cyano-4-(2,3-dichlorophenyl)-pyrrole, possess fungicidal activity (cf., for example, EP No. 236,272).

However, the activity of these previously known compounds is not completely satisfactory in all fields of application, in particular at low application rates and when low concentrations are used.

New 3-cyano-4-phenyl-pyrrole derivatives of the general formula (I)

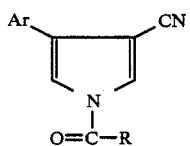

in which
Ar stands for phenyl which is trisubstituted to pentasubstituted and
R stands for alkyl, alkoxy or alkoxyalkyl, have been found.

Furthermore, it has been found that the new 3-cyano-4-phenyl-pyrrole derivatives of the general formula (I)

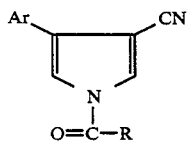

in which
Ar stands for phenyl which is trisubstituted to pentasubstituted and
R stands for alkyl, alkoxy or alkoxyalkyl, are obtained when 1H-3-cyano-4-phenyl-pyrroles of the formula (II)

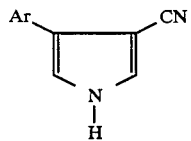

in which
Ar has the abovementioned meaning, are reacted with acylating agents of the formula (III)

in which
R has the abovementioned meaning and
E stands for an electron-withdrawing leaving group, if appropriate in the presence of a diluent and if appropriate in the presence of a reaction auxiliary.

Finally, it has been found that the new 3-cyano-4-phenyl-pyrrole derivatives of the general formula (I) possess a good action against pests.

Surprisingly-, the 3-cyano-4-phenyl-pyrrole derivatives of the general formula (I) according to the invention, for example, show a considerably better fungicidal activity than the 3-cyano-4-phenyl-pyrroles, such as, for example, the compound 3-cyano-4-(2,3-dichlorophenyl)-pyrrole, which are known from the prior art and are chemically similar compounds of a similar type of action.

Formula (I) provides a general definition of the 3-cyano-4-phenyl-pyrrole derivatives according to the invention. Preferred compounds of the formula (I) are those in which Ar stands for phenyl which is trisubstituted to pentasubstituted by identical or different substituents, substituents which may be mentioned being: halogen, in particular fluorine, chlorine or bromine, in each case straight-chain or branched alkyl, alkoxy or alkylthio, each having 1 to 4 carbon atoms, in each case straight-chain or branched halogenoalkyl, halogenoalkoxy or halogenoalkylthio, each having 1 to 4 carbon atoms and 1 to 9 identical or different halogen atoms, in each case double-linked dioxyalkylene or halogenodioxyalkylene, each having 1 or 2 carbon atoms and if appropriate 1 to 4 identical or different halogen atoms and R stands for in each case straight-chain or branched alkyl, alkoxy or alkoxyalkyl, each having 1 to 6 carbon atoms in the individual alkyl moieties.

Particularly preferred compounds of the formula (I) are those in which

Ar stands for phenyl which is tri- or tetrasubstituted by identical or different substituents, the following substituents being particularly preferred: fluorine, chlorine, bromine, methyl, methoxy, methylthio, trifluoromethyl, trifluoromethoxy, trifluoromethylthio, in each case double-linked dioxymethylene or difluorodioxymethylene and R stands for in each case straight-chain or branched alkyl, alkoxy or alkoxyalkyl, each having 1 to 4 carbon atoms in the individual alkyl moieties.

Very particularly preferred compounds of the formula (I) are those in which

Ar stands for phenyl which is tri- or tetrasubstituted by identical or different substituents, at least one of the substituents being fluorine and suitable other substituents being: chlorine, bromine, methyl, methoxy, methylthio, trifluoromethyl, trifluoromethoxy, trifluoromethylthio or difluorodioxymethylene and R stands for methyl, ethyl, methoxy, ethoxy, methoxymethyl or ethoxymethyl.

In addition to the compounds mentioned in the Preparation Examples, the following 3-cyano-4-phenyl-pyrrole derivatives of the general formula (I) may be mentioned individually:

$$\underset{\underset{O=C-R}{\overset{|}{N}}}{\text{Ar}}\underset{}{\overset{\text{CN}}{\diagdown}} \quad (I)$$

| Ar | R | Ar | R |
|---|---|---|---|
| 2-Cl, 3-F, 5-F, 6-F phenyl | —VCH₃ | 2-F, 3-Cl, 5-F, 6-F phenyl | —CH₂—OC₂H₅ |
| 2-CF₃, 3-F, 5-F, 6-F phenyl | —CH₃ | 2-F, 3-Cl, 5-F, 6-F phenyl | —OC₂H₅ |
| 2-CF₃, 3-Cl, 5-F phenyl | —CH₃ | 2-Cl, 3-Cl, 5-F phenyl | —CH₃ |
| 2-Cl, 3-CF₃, 5-F, 6-F phenyl | —CH₂—OCH₃ | 2-Cl, 3-Cl, 5-F phenyl | —OCH₃ |
| 2-Cl, 3-CF₃, 5-F phenyl | —OC₂H₅ | 2-Cl, 3-Cl, 5-F phenyl | —CH₂—O—CH₃ |
| 2-Cl, 3-CF₃, 5-F phenyl | —OC₂H₅ | 2-Cl, 3-F, 5-F phenyl | —CH₃ |
| 2-CF₃, 3-Cl, 5-F phenyl | —OCH₃ | 2-Cl, 3-F, 5-F phenyl | —OCH₃ |
| 2-OCF₃, 3-Cl, 5-F phenyl | —OC₂H₅ | 2-Cl, 3-F, 5-F phenyl | —CH₂—OCH₃ |

-continued

| Ar | R | Ar | R |
|---|---|---|---|
| 4-F, 3-F, 2-OCF₃ phenyl (2,4-difluoro-... with OCF₃) | $-O-(CH_2)_3-CH_3$ | 2-F₃C, 3-F, 6-CF₃ phenyl | $-CH_3$ |
| 2-Cl, 4-F, 5-F, 6-SCF₃ phenyl | $-O-(CH_2)_2-CH_3$ | | |
| 2-Cl, 3-F, 4-F, 6-F phenyl | $-C_2H_5$ | | |

If, for example, 3-cyano-4-(2,4-difluoro-3-chlorophenyl)-pyrrole and ethyl chloroformate are used as starting substances, the course of the reaction of the process according to the invention may be represented by the following equation:

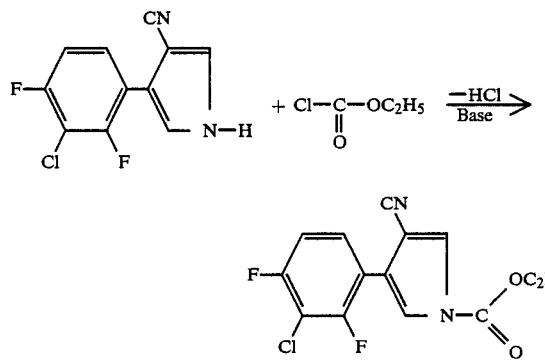

Formula (II) provides a general definition of the 1H-3-cyano-4-phenylpyrroles required as starting substances for carrying out the process according to the invention. In this formula (II), Ar preferably stands for those radicals which have already been mentioned in connection with the description of the substances of the formula (I) according to the invention as being preferred for this substituent.

The 1H-3-cyano-4-phenylpyrroles of the formula (II) are the subject-matter of German Patent Application No. P 3,737,983 filed Nov. 9, 1987, corresponding to U.S. application Ser. No. 266,468, filed Nov. 2, 1988, now pending, and they can be obtained in analogy to known processes (cf., for example, EP No. 236,272, DE-OS (German Published Specification) No. 2,927,480), for example in a process in which (a) substituted anilines of the formula (IV)

$$Ar-NH_2 \quad (IV)$$

in which

Ar has the abovementioned meaning, are initially reacted in a first step with acrylonitrile under customary diazotization conditions, for example in the presence of sodium nitrite and hydrochloric acid, and in the presence of a suitable metal salt catalyst, such as, for example, copper(II) chloride or copper(II) oxide, and if appropriate in the presence of a suitable diluent, such as, for example, acetone or water, at temperatures between −20° C. and 50°C. ("Meerwein Arylation"; cf. in this context also Organic Reactions 11, 189 [1960]; Organic Reactions 24, 225 [1976] or C. Ferri "Reaktionen der organischen Synthese" [Reactions of Organic Synthesis] p. 319, Thieme Verlag Stuttgart 1978) and the resulting substituted α-chloro-β-phenylpropionitriles of the formula (V)

in which

Ar has the abovementioned meaning, are then dehydrohalogenated in a second step with bases, such as, for example, triethylamine or diazabicycloundecene, in a customary manner, if appropriate in the presence of a diluent, such as, for example, tetrahydrofuran, at temperatures between 0° C. and 50° C. (cf. also the Preparation Examples), or, alternatively, in which (b) substituted benzaldehydes of the formula (VI)

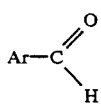 (VI)

in which

Ar has the abovementioned meaning, are condensed with cyanoacetic acid of the formula (VII)

NC—CH₂—COOH (VII)

in a customary manner in the presence of a base, such as, for example, piperidine or pyridine, and if appropriate in the presence of a suitable diluent, such as, for example, pyridine, at temperatures between 50° C. and 120° C., and simultaneously decarboxylated (cf., for example, "Organikum" [Laboratory Practice of Organic Chemistry] p. 571/572; 15th edition; VEB Deutscher Verlag der Wissenschaften Berlin 1981 and also the Preparation Examples), and the resulting [from process (a) or (b)] substituted cinnamonitriles of the formula (VIII)

Ar—CH=CH—CN (VIII)

in which

Ar has the abovementioned meaning, are reacted with sulphonylmethyl isocyanides of the formula (IX)

R¹—SO₂—CH₂—NC (IX)

in which

R¹ stands for alkyl or for optionally substituted aryl, in particular for methyl, for 4-methylphenyl, 4-chlorophenyl or for phenyl, in the presence of a base, such as, for example, sodium
hydride and if appropriate in the presence of a diluent, such as, for example, tetrahydrofuran, at temperatures between −20° C. and +50° C.

Some of the substituted anilines of the formula (IV) are known (cf., for example, J. Org. Chem. 39, 1758-1761 [1974]; J. med. Chem. 12, 195-196 [1969] or U.S. Pat. No. 3,900,519).

New compounds are for example the substituted anilines of the formula (IVa)

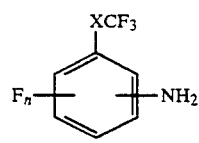 (IVa)

in which

X stands for oxygen or sulphur and
n stands for 2.

They form the subject-matter of German Patent Application No. P 3,737,985, filed Nov. 9, 1987, corresponding to U.S. application Ser. No. 264,462, filed Oct. 28, 1988, now pending.

A generally applicable process for the preparation of compounds of the formula (IVa)

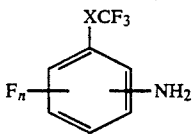 (IVa)

in which

X stands for oxygen or sulphur and
n stands for 2, is characterized in that compounds of the formula (X)

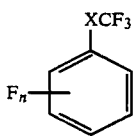 (X)

in which

X and n have the abovementioned meaning, are nitrated and the resulting nitro compounds are reduced.

The fluorine-containing trifluoromethoxy- or trifluoromethylthiobenzenes of the formula (X) which are to be employed in this process are known (cf., for example, J. Fluorine Chem. 2,387-398 [1973]; Tetrahedron Lett. 1973, 2253-2256; Zh. Org. Khim. 12, 1183-1187 [1976]; J. chem. Soc. Perkin Trans. I, 1972, 2180-2182).

Nitrating can be carried out using customary nitrating agents, for example mixtures of nitric acid and sulphuric acid. In this process, the temperature can be, for example, in the range 0° to 80° C., it is preferably at 20° to 50° C. The nitrating agent can be employed for example in amounts resulting in the formation of 0.8 to 1.5 moles of nitrating agent per mole of starting compound in the reaction mixture. Preferably, 1 to 1.1 moles of nitrating agent are allowed to form per mole of starting compound. If appropriate, the nitration can be carried out in the presence of an inert organic solvent. A suitable example is methylene chloride.

The subsequent reduction can be carried out chemically, i.e., for example, using metals or metal salts having a reducing action. Suitable examples are iron, zinc, tin, tin(II) chloride or titanium(III) chloride. Reducing agents of this type are preferably employed in the stoichiometrically required amount. For a reduction of this type, the nitro compounds can be employed, for example, as they are obtained in the nitration process, or they can be isolated afterwards. The reduction can also be carried out catalytically using hydrogen, it being possible, for example, to employ catalysts which contain metals or consist of them. Examples of suitable metals are those of subgroup VIII of the Periodic Table of the Elements, in particular palladium, platinum and nickel. The metals can be present in elementary form or in the form of compounds, and also in particularly activated forms, for example in the form of Raney metals, or they can be fixed to support materials as metal or metal compound. Raney nickel or palladium on charcoal or aluminum oxide is preferred.

The catalytic reduction is preferably carried out in the presence of a solvent. Suitable examples are alcohols or ethers, such as methanol, ethanol or tetrahydrofuran. For example, the catalytic reduction can be carried out at temperatures in the range 0° to 80° C. and at hydrogen pressures in the range 1 to 100 bar. In general, excess hydrogen does not impair the reaction.

Acid-free nitro compounds are preferably employed for the catalytic reduction. If appropriate, the latter must thus be freed from acids, for example by washing with water or neutralization with bases, such as, for example, sodium hydrogen carbonate.

Working up of the reaction mixture which is present after the chemical reduction or the catalytic hydrogenation can be carried out for example in a manner such that any solid constituents are initially filtered off and the filtrate is distilled, if appropriate after washing with water. In the event that an isomer mixture is obtained as the reaction product, the former can be resolved by precision distillation.

Compounds of the formula (IVa) having fluorine in o- and p-position relative to the amino group can also be prepared by a process in which compounds of the formula (XI)

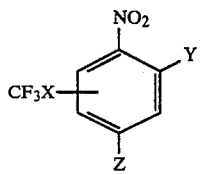

in which

X stands for oxygen or sulphur and

Y and Z in each case stand for chlorine, are reacted with potassium fluoride in the presence of tetramethylenesulphone, during which process the chlorine present is replaced by fluorine, and a reduction is subsequently carried out in which the nitro group is converted to an amino group.

Compounds of the formula (XI) are known (cf. Houben-Weyl, Methoden der organischen Chemie [Methods of Organic Chemistry] E 4, p. 633 et seq.; Chem. Ber. 96, 48–55 [1963]).

For example, 0.5 to 3 moles of potassium fluoride can be employed per equivalent of chlorine to be exchanged for fluorine, in the compound of the formula (XI). This amount is preferably 1.2 to 1.5 moles. Tetramethylenesulphone acts as a solvent and is preferably employed in at least an amount such that a reaction mixture is present which can readily be stirred. Relatively large amounts of solvent do not interfere with the reaction.

Suitable temperatures for the reaction with potassium fluoride in tetramethylene sulphone are for example those in the range 160° to 230° C. Preferred temperatures are those from 180° to 210° C. Preferably, the reaction is carried out in an environment which is as anhydrous as possible. This can be achieved, for example, by employing the compound of the formula (XI) in carefully dried form as the last component and by distilling off a small amount of tetramethylenesulphone together with any water present from the other previously added components.

When the reaction is complete, solids present in the reaction mixture and if appropriate all or some of the tetramethylenesulphone can be removed. The subsequent reduction of the nitro group to give the amino group and the working up of the then present reaction mixture can be carried out as has been described before in the generally applicable process for the preparation of the compounds of the formula (IVa).

Alternatively, compounds of the formula (IVa) in which X stands for oxygen can be prepared by a process in which compounds of the formula (XII)

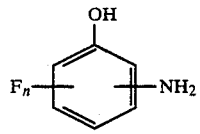

in which n stands for 2, is reacted with carbon tetrachloride in the presence of hydrogen fluoride, during which process the OH group is converted to a $F_3CO$ group.

Compounds of the formula (XII) are known (cf. FR Pat. No. 2,446,805).

For example, 1 to 10 moles of carbon tetrachloride and 5 to 30 moles of hydrogen fluoride can be employed per mole of the specific compound of the formula (XII). Even relatively large excesses of carbon tetrachloride and hydrogen fluoride generally do not interfere with the reaction. Suitable reaction temperatures are for example those in the range 100° to 150° C. This process is preferably carried out under pressure, for example by not releasing the resulting hydrogen chloride gas before a certain pressure. For example, this pressure can be between 18 to 60 bar. If appropriate, an inert gas can additionally be injected, for example 1 to 20 bar nitrogen. It is advantageous to stir well during the reaction.

Working up of the reaction mixture can be carried out for example by cooling the reaction mixture to room temperature, releasing it, distilling off excess hydrogen fluoride and excess carbon tetrachloride, for example at temperatures up to 80° C., placing the residue on ice water, rendering the mixture alkaline using sodium hydroxide solution, and extracting the organic phase using dichloromethane and subjecting it to precision distillation after drying.

Other new fluorine- and/or chlorine-containing trifluoromethylaminobenzenes are those in which the trifluoromethyl group is in the 1-position and (a) the amino group is in the 2-position and two fluorine atoms are in the 5- and 6-positions or one fluorine atom is in the 5-position and one chlorine atom is in the 6-position or (b) the amino group is in the 3-position and two fluorine atoms are in the 2- and 6-positions or one chlorine atom is in the 2-position and one fluorine atom in the 6-position or (c) the amino group is in the 4-position and one fluorine atom is in the 2-position and, additionally, one more fluorine atom is in the 3- or 6-position or two more fluorine atoms are in the 5- and 6-positions or one more fluorine atom is in the 6-position and two chlorine atoms are in the 3- and 5-positions or one chlorine atom is in the 3-position or two chlorine atoms are in the 3- and 5-positions or (d) the amino group is in the 4-position and two fluorine atoms are in the 3- and 5-positions or two chlorine atoms are in the 2- and 3-positions or one fluorine atom is in the 3-position and one chlorine atom in the 5-position.

These amines form the subject-matter of German Patent Application No. P3,737,986, filed Nov. 9, 1987, corresponding to U.S. application Ser. No. 261,795, filed Oct. 24, 1988, now pending.

In detail, these amines are 2-amino-5,6-difluorobenzotrifluoride, 2-amino-5-fluoro-6-chloro-benzotrifluoride, 2,6-difluoro-3-amino-benzotrifluoride, 2-chloro-3-amino-6-fluoro-benzotrifluoride, 2,3-difluoro- 4-amino-benzotrifluoride, 2,6-difluoro-4-amino-benzotrifluoride, 2,5,6-trifluoro-4-amino-benzotrifluoride, 2,6-difluoro-3,5-dichloro-4-amino-benzotrifluoride, 2-fluoro-3-chloro-4-amino-benzotrifluoride, 2-fluoro-3,5-dichloro-4-amino-benzotrifluoride, 3,5-difluoro-4-amino-benzotrifluoride, 2,3-dichloro-4-amino-benzotrifluoride and 3-fluoro-4-amino-5-chloro-benzotrifluoride.

A preferred process for the preparation of fluorine- and/or chlorine-containing trifluoromethylaminobenzenes in which the trifluoromethyl group is in the 1-position and
(a) the amino group is in the 2-position and two fluorine atoms are in the 5- and 6-positions or one fluorine atom is in the 5-position and one chlorine atom is in the 6-position or
(b) the amino group is in the 3-position and two fluorine atoms are in the 2- and 6-position or one chlorine atom is in the 2-position and one fluorine atom in the 6-position or
(c) the amino group is in the 4-position and one fluorine atom is in the 2-position and, additionally, one more fluorine atom is in the 3- or 6-position or two more fluorine atoms are in the 5- and 6-position or one more fluorine atom is in the 6-position and two chlorine atoms are in the 3- and 5-position or one chlorine atom is in the 3-postion or two chlorine atoms are in the 3- and 5-positions or
(d) the amino group is in the 4-position and two fluorine atoms are in the 3- and 5-positions or two chlorine atoms are in the 2- and 3-position or one fluorine atom is in the 3-position and one chlorine atom in the 5-position
is characterized in that corresponding fluorine- and/or chlorine-containing trifluoromethylbenzenes are nitrated and the resulting fluorine- and/or chlorine-containing trifluoromethylnitrobenzenes are reduced.

The fluorine- and/or chlorine-containing trifluoromethylbenzenes which, however, are free of amino groups and which are to be employed in this process are known [cf., for example, J. Chem. Soc. C, (8), 1547–9 (1971)].

The nitration can be carried out using customary nitrating agents, for example using mixtures of nitric acid and sulphuric acid. In this process, the temperature can for example be in the range 0° to 80° C., preferably it is at 20° to 50° C. The nitrating agent can be employed for example in amounts which result in the formation of 0.8 to 1.5 moles of nitrating agent in the reaction mixture per mole of starting compound. Preferably, an amount of nitrating agent is employed which results in the formation of 1 to 1.1 moles of nitrating agent per mole of starting compound. If appropriate, the nitration can be carried out in the presence of an inert organic solvent. A suitable example is methylene chloride.

The subsequent reduction can be carried out chemically, i.e., for example using metals or metal salts having a reducing action. Suitable examples are iron, zinc, tin, tin(II) chloride and titanium(III) chloride. Reducing agents of this type are preferably employed in the stoichiometrically required amount. For a reduction of this type, the nitro compounds can be employed, for example, as they are obtained in the nitration or in the purified form.

The reduction can also be carried out catalytically using hydrogen, in which process it is possible, for example, to employ catalysts containing metals or consisting thereof. Suitable metals are, for example, subgroup VIII of the Periodic Table of the Elements, in particular palladium, platinum and nickel. The metals can be present in elementary form or in the form of compounds, and also in particularly activated forms, for example in the form of Raney metals, or as a metal or metal compound fixed to support materials. Raney nickel or palladium on charcoal or aluminum oxide is preferred.

The catalytic reduction is preferably carried out in the presence of a solvent. Suitable examples are alcohols and ethers, such as methanol, ethanol or tetrahydrofuran. The catalytic reduction can be carried out for example at temperatures in the range 10° to 60° C. and for example at hydrogen pressures in the range 1 to 100 bar. In general, excess hydrogen does not interfere with the reaction.

Preferably, acid-free nitro compounds are employed for the catalytic reduction. If necessary, they must thus be freed from acids after the preparation, for example by washing with water or by neutralization with bases, such as, for example, sodium hydrogen carbonate.

Working up of the reaction mixture present after the chemical reduction or the catalytic hydrogenation can be carried out for example in a manner such that initially, if appropriate, any solid constituents present are filtered off and the filtrate is washed with water, if appropriate, and then distilled. In the event that an isomer mixture is obtained as the reaction product, the former can be resolved by precision distillation, if required.

A variant of the previously described catalytic reduction is carried out in the presence of a base, for example in the presence of alkali metal hydroxides or alkali metal carbonates or of tertiary amines. Tertiary amines, such as triethylamine or pyridine, are preferred. Using in each case one equivalent of base per mole of the nitro compound employed in the catalytic reduction, one additional equivalent of chlorine atoms can be set free from the former during the catalytic reduction. Thus, for example, a chlorine-free, fluorine-containing aminobenzotrifluoride can be obtained from a fluorine- and chlorine-containing nitrobenzotrifluoride.

A further process specifically for the preparation of fluorine- and/or chlorine-containing trifluoromethylaminobenzenes in which the trifluoromethyl group is in the 1-position and
(a') the amino group is in the 2-position and two fluorine atoms are in the 5- and 6-positions or one fluorine atom is in the 5-position and one chlorine atom in the 6-position or
(b') the amino group is in the 4-position and one fluorine atom in the 2-position and, additionally, another fluorine atom is in the 3- or 6-position or two other fluorine atoms are in the 5- and 6-position or one more fluorine atom is in the 6-position and two chlorine atoms are in the 3- and 5-position or one chlorine atom is in the 3-position or two chlorine atoms are in the 3- and 5-position or
(c') the amino group is in the 4-position and two fluorine atoms are in the 3- and 5-positions or two chlorine atoms are in the 2- and 3-positions or one fluorine atom is in the 3-position and one chlorine atom in the 5-position
is characterized in that corresponding fluorine- and/or chlorine-containing 2- and/or 4-halogeno-trifluoromethylbenzenes are reacted with ammonia under increased pressure and in the presence of an organic solvent.

The 2- and/or 4-halogeno-trifluoromethylbenzenes to be employed in this process are known (cf. EP No. 34,402).

The ammonia can be added in liquid or gaseous form, for example as the substance itself (gaseous or liquid) or as aqueous solution. For example, 1 to 10 moles of ammonia can be used per mole of halogen atoms to be substituted by NH₂ groups in the 2- and/or 4-position. This amount is preferably 3 to 8 moles. Suitable temperatures for this reaction are for example those in the range 80° to 160° C., those in the range 100° to 130° C. being preferred. The reaction can be carried out under the inherent pressure of the ammonia arising in the sealed vessel at the reaction temperature, which pressure can for example be in the range 10 to 20 bar. It is also possible to apply higher pressures, for example those up to 100 bar.

Solvents for this reaction which can be employed are inert or essentially inert organic solvents of a very wide variety. Examples of suitable solvents are: alcohols, ethers, sulphones and aromatic hydrocarbons.

The desired reaction product(s) can be obtained from the reaction mixture present after the reaction for example by initially cooling the mixture and releasing the pressure, then removing the solvent and subsequently carrying out a distillation, preferably under reduced pressure.

Most of the fluorobenzaldehydes of the formula (VI) also required as precursors for the preparation of the new starting materials of the formula (II) following variant (b) are known (cf., for example, Jap. Pat. No. 58-222,045 or C.A. 100: 209,288k), and cyanoacetic acid of the formula (VII) is likewise generally known (cf. Laboratory Practice of Organic Chemistry "Organisch-chemisches Grundpraktikum [Basic Laboratory Practice of Organic Chemistry]", Berlin 1977, VEB Deutscher Verlag der Wissenschaften, page 573).

The sulphonylmethyl isocyanides of the formula (IX) also required as precursors for the preparation of the new starting materials of the formula (II) are likewise known (cf., for example, Synthesis 1985, 400–402; Org. Syntheses 57, 102–106 [1977]; J. org. Chem. 42, 1153–1159 [1977]; Tetrahedron Lett. 1972, 2367–2368).

Formula (III) provides a general definition of the acylating agents also required as starting substances for carrying out the process according to the invention. In this formula (III), R preferably stands for those radicals which have already been mentioned in connection with the description of the substances of the formula (I) according to the invention as preferred for this substituent.

E preferably stands for halogen, in particular for chlorine or bromine, or for an anhydride radical of formula

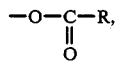

where R has the abovementioned meaning.

The acylating agents of the formula (III) are generally known compounds of organic chemistry.

As an alternative for the preparation of the precursors of the formula (II) with the aid of the previously described preparation processes, various other preparation processes for the preparation of the precursors of the formula (II) are feasible.

Thus, 1H-3-cyano-4-phenyl-pyrroles of the formula (II) can also be obtained, for example, when α-cyanocinnamic acid esters are reacted with p-toluenesulphonylmethyl isocyanide in the presence of bases and in the presence of copper(II) salts (of. JP No. 61/030, 571 or JP No. 61/200, 984) or when α-substituted cinnamonitriles are cyclized with isocyanoacetic acid esters in the presence of sodium hydride, the resulting pyrrole-2-carboxylic acid esters are hydrolyzed with bases and subsequently thermally decarboxylated (cf. JP No. 59/212,468) or when phenacylamine derivatives are reacted with suitably substituted acrylonitrile derivatives (cf. EP No. 174,910) or when 3-trifluoromethyl-4-phenyl-pyrroles are reacted with ammonia at increased temperature and under increased pressure (cf. EP No. 182,738) or when 3-cyano-4-phenyl-Δ²-pyrrolines are oxidized in the presence of copper(II) salts or iron(III) salts (cf. EP No. 183,217) or when αcyanoacrylic acid derivatives are reacted with isocyanoacetic acid esters in the presence of a base and the resulting Δ²-pyrroline-2-carboxylic acid derivatives are oxidatively decarboxylated in a second step in the presence of a base and in the presence of a metal salt catalyst (cf. German Patent Application No. P 3,718,375 dated 02.06.1987).

Suitable diluents for carrying out the process according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

The process according to the invention is preferably carried out in the presence of a suitable reaction auxiliary. Suitable reaction auxiliaries are all customary inorganic or organic bases. These preferably include alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimeethylaniline, pyridine, N,N-dimethylaminopyridine, diazabicyclooctane (DABCO), diazabicyclononene (DBN) or diazabicycloundecene (DBU).

When carrying out the process according to the invention, the reaction temperatures can be varied within a relatively wide range. In general, the process is carried out at temperatures between −20° C. and 150° C., preferably at temperatures between 0° C. and 80° C.

For carrying out the process$s according to the invention, 1.0 to 5.0 moles, preferably 1.0 to 1.5 moles, of acylating agent of the formula (III) and if appropriate 1.0 to 5.0 moles, preferably 1.0 to 1.5 moles, of reaction auxiliary are generally employed per mole of 1H-3-cyano-4-phenyl-pyrrole of the formula (II).

The reaction is carried out, and the reaction products are worked up and isolated by generally customary methods (cf. also the Preparation Examples).

The active compounds according to the invention exhibit a powerful action against pests and can be employed in practice for combating undesired pests. The active compounds are suitable, inter alia, for the use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, Sphaerotheca fuliginea; Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

Here, the active compounds according to the invention can be employed with particularly good success for combating diseases in fruit growing and vegetable growing, such as, for example, against the causative organism of grey mould of beans (*Botrytis cinerea*), or for combating rice diseases, such as, for example, against the causative organism of rice blast disease (*Pyricularia oryzae*) or for combating cereal diseases, such as, for example, against the causative organism of leaf spot of wheat (*Leptosphaeria nodorum*) or against the causative organism of net blotch of barley (*Pyrenophora teres*) or against the causative organism of cereal snow mould (*Fusarium nivale*). Furthermore, the active compounds according to the invention possess a good fungicidal activity in vitro.

Depending on their respective physical and/or chemical properties the active compounds can be converted to the customary formulations, such as solutions, emulsions, suspensions, powders, foams, pastes, granules, aerosols, very fine capsules in polymeric substances and in coating compositions for seed, as well as ULV hot and cold mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products. As dispersing agents there are suitable, for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

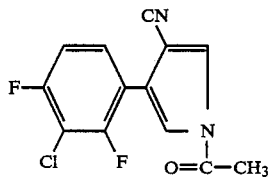

0.63 g (0.0062 mole) of acetic anhydride, 0.62 g (0.0062 mole) of triethylamine and 0.1 g of 4-dimethylaminopyridine are added to 1.4 g (0.006 mole) of 3-cyano-4-(2,4-difluoro-3-chlorophenyl)-pyrrole in a mixture of 50 ml of dichloromethane/tetrahydrofuran (4:1), the mixture is stirred for 16 hours at room temperature, washed twice with water, dried over sodium sulphate and evaporated in vacuo.

1.5 g (90% of theory) of 1-acetyl-3-cyano-4-(2,4-difluoro-3-chlorophenyl)-pyrrole of melting point 182° C.-183° C. are obtained.

Example 2

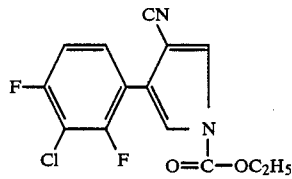

4.3 g (0.018 mole) of 3-cyano-4-(2,4-difluoro-3-chlorophenyl)-pyrrole in 60 ml of dimethoxyethane are added dropwise and with stirring to 0.65 g (0.022 mole) of sodium hydride (80 percent strength in paraffin oil) in 20 ml of dimethoxyethane, and stirring is then continued at room temperature for two more hours. 3.4 g (0.032 mole) of ethyl chloroformate, dissolved in 20 ml of dimethoxyethane, are then added dropwise to the stirred mixture, likewise at room temperature, the mixture is stirred at room temperature for 3 more hours, hydrolyzed with water, extracted using ethyl acetate, washed twice with water and dried over sodium sulphate, and the solvent is removed in vacuo.

5.3 g (94% of theory) of 1-ethoxycarbonyl-3-cyano-4-(2,4-difluoro-3-chlorophenyl)-pyrrole of melting point 132° C. are obtained.

PREPARATION OF THE STARTING COMPOUND

Example II-1

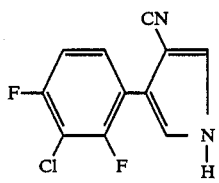

A solution of 6.0 g (0.03 mole) of 3-(2,4-di fluoro-3-chlorophenyl)-acrylonitrile and 7.8 g (0.0431 mole) of p-toluenesulphonylmethyl isocyanide in 20 ml of a mixture of tetrahydrofuran/dimethyl sulphoxide (5:1) is added dropwise, with stirring, at −10° C. to −20° C. and under an argon gas protective atmosphere to 1.3 g (0.0431 mole) of sodium hydride (80% strength in mineral oil) in 16 ml of tetrahydrofuran. When the addition is complete, the reaction mixture is allowed to reach room temperature, water is added, the mixture is extracted several times using ethyl acetate, and the combined ethyl acetate phases are washed with water, dried over sodium sulphate and evaporated in vacuo. The residue is purified by chromatography on silica gel (eluent: cyclohexane/ethyl acetate 5:1).

4.8 g (67% of theory) of 3-cyano-4-(2,4-difluoro-3-chlorophenyl)-pyrrole of melting point 218° C.-219° C. are obtained.

Example VIII-1

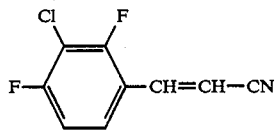

18.2 g (0.12 mole) of diazabicycloundecene in 150 ml of tetrahydrofuran are added dropwise, at room temperature and with stirring, to 25.5 g (0.11 mole) of 2-chloro-3-(2,4-difluoro-3-chlorophenyl)-propionitrile in 100 ml of tetrahydrofuran. When the addition is complete, the mixture is stirred at room temperature for 15 hours and filtered, the filtrate is evaporated in vacuo, the residue is taken up in ethyl acetate, the mixture is washed in succession with 1 normal hydrochloric acid and water and dried over sodium sulphate, and the solvent is removed in vacuo.

20.6 g (94% of theory) of 3-(2,4-difluoro-3-chlorophenyl)-acrylonitrile of melting point 76° C. -77° C. are obtained.

Example V-1

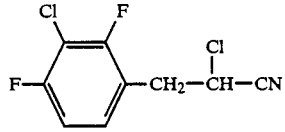

40 ml of 25 percent hydrochloric acid and 28.8 ml (0.37 mole) of acrylonitrile are added to 20.0 g (0.12 mole) of 2,4-difluoro-3-chloro-aniline (cf., for example, J. Fluorine Chem. 2, 19-26 [1972]) in 40 ml of acetone, 8.7 g (0.13 mole) of sodium nitrite in 17 ml of water are then added at 0° C. to 10° C. in the course of one hour and with stirring, the mixture is stirred for one more hour at 0° C. to 10° C., and several portions copper(II) oxide powder are then added, during which reaction vigorous evolution of nitrogen can be observed. When the evolution of gas is complete, the mixture is stirred at room temperature for 15 more hours, dichloromethane is then added, the mixture is washed with water, dried over sodium sulphate and evaporated in vacuo, and the residue is purified by distillation under a high vacuum.

25.5 g (90% of theory) of 2-chloro-3-(2,4-di-fluoro-3-chlorophenyl)-propionitrile of boiling point 75°–77° C. at 0.15 mbar are obtained.

The following 3-cyano-4-phenyl-pyrrole derivative of the general formula (I)

is obtained in a corresponding manner and &following the general instructions for preparation:

| Example No. | Ar | R | Melting point [°C.] |
|---|---|---|---|
| 3 | (F, Cl, F trisubstituted phenyl) | —CH$_2$—OCH$_3$ | 144–145 |

Use Examples

In the following Use Examples, the compounds listed below were employed as comparison substances:

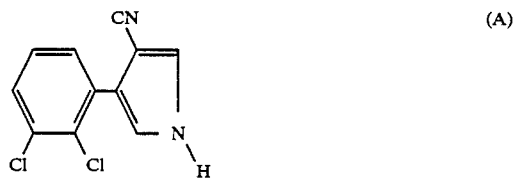

3-Cyano-4-(2,3-dichlorophenyl)-pyrrole (cf. EP Nos. 174,910 and 236,272).

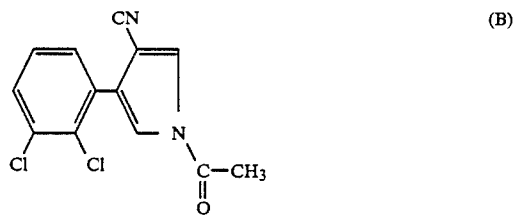

1-Acetyl-3-cyano-4-(2,3-dichlorophenyl)-pyrrole (cf. DE-OS (German Published Specification) No. 2,927,480).

Example A

Botrytis test (bean)/protective
Solvent: 4.7 parts by weight
Emulsifier: 0.3 part by weight To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, a clearly superior activity compared with the prior art is shown, for example by the compounds according to Preparation Examples 1 and 3.

Example B

*Leptosphaeria nodorum* test (wheat)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to Preparation Examples 1 and 3.

It will be appreciated that the instant specification and claims are set forth by way of illustration and not limitation, and that various modifications and changes may be made without departing from the spirit and scope of the present invention.

We claim:

1. A 3-cyano-4-phenyl-pyrrole of the formula

in which
Ar stands for phenyl which is trisubstituted by halogen, at least one of which is fluorine, and
R stands for in each case straight-chain or branched alkyl, alkoxy or alkoxyalkyl each having 1 to 6 carbon atoms in the individual alkyl moieties.

2. A 3-cyano-4-phenyl-pyrrole according to claim 1, in which
R stands for in each case straight-chain or branched alkyl, alkoxy or alkoxyalkyl each having 1 to 4 carbon atoms in the individual alkyl moieties.

3. A 3-cyano-4-phenyl-pyrrole according to claim 1, in which

R stands for methyl, ethyl, methoxy, ethoxy, methoxymethyl or ethoxymethyl.

4. A compound according to claim 1, wherein such compound is 1-acetyl-3-cyano-4-(2,4-difluoro-3-chlorophenyl)-pyrrole of the formula

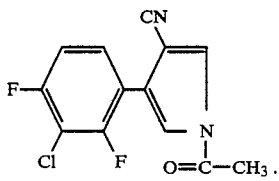

5. A compound according to claim 1, wherein such compound is 1-ethoxycarbonyl-3-cyano-4-(2,4-difluoro-3-chlorophenyl)-pyrrole of the formula

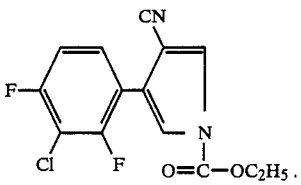

6. A compound according to claim 1, wherein such compound is 1-methoxymethylcarbonyl-3-cyano-4-(2,4-difluoro-3-chlorophenyl)-pyrrole of the formula

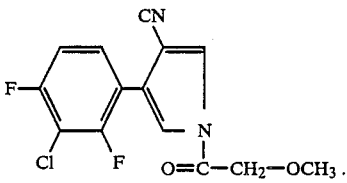

7. A fungicidal composition comprising a fungicidally effective amount of a compound according to claim 1 and a diluent.

8. A method of combating fungi which comprises applying to such fungi or to a fungus habitat a fungicidally effective amount of a compound according to claim 1.

9. The method according to claim 8, wherein such compound is
1-acetyl-3-cyano-4-(2,4-difluoro-3-chlorophenyl)-pyrrole,
1-ethoxycarbonyl-3-cyano4-(2,4-difluoro-3-chlorophenyl)-pyrrole, or
1-methoxymethylcarbonyl-3-cyano-4-(2,4-difluoro-3-chlorophenyl)-pyrrole.

* * * * *